United States Patent [19]

Sato et al.

[11] Patent Number: 5,389,630

[45] Date of Patent: Feb. 14, 1995

[54] DIAMINE COMPOUND AND BRAIN PROTECTING AGENT CONTAINING THE SAME

[75] Inventors: Seiichi Sato, Tokyo; Kiyoshi Kawamura, Niiza; Yoshio Takahashi, Iruma; Koichiro Watanabe, Kawajima; Sadahiro Shimizu; Tomio Ohta, both of Sayama, all of Japan

[73] Assignee: Kowa Co., Ltd., Nagoya, Japan

[21] Appl. No.: 966,142

[22] PCT Filed: Jul. 30, 1990

[86] PCT No.: PCT/JP90/00970

§ 371 Date: Jan. 22, 1993

§ 102(e) Date: Jan. 22, 1993

[87] PCT Pub. No.: WO92/02487

PCT Pub. Date: Feb. 20, 1992

[51] Int. Cl.$^6$ .................... C07D 243/08; A61K 31/55
[52] U.S. Cl. .................... 514/218; 540/575; 540/470; 544/398; 544/399; 544/400; 544/402; 544/403; 548/300.1; 564/336; 564/372
[58] Field of Search .................... 540/575; 514/218

[56] References Cited

U.S. PATENT DOCUMENTS 4,661,481  4/1987  Devlin et al. .................... 540/575

FOREIGN PATENT DOCUMENTS 0129207  12/1984  European Pat. Off. .
152598   8/1985  European Pat. Off. .
0330065  8/1989  European Pat. Off. .
57-32255  2/1982  Japan .

OTHER PUBLICATIONS

Janssen Pharm. N.V., Chemical Abstract vol. 64, No. 12704g (1966) for Netherlands Appl 6,507,312.
Kotelko et al., Chem. Abstract 71:38928n (1969).
Majchrzale et al, Chem. Abstract 99:5610c (1983).
Burger, editor, *Medicinal Chemistry*, 3rd ed. (1970), part I pp. 74–75.
Noller, *Chemistry of Organic Compounds*, 2nd ed (1957), p. 272.
*Journal of Pharmaceutical Sciences*, 3 pgs., vol. 72, No. 3, Mar. 1983, *Synthesis and Action on the Central Nervous System of Mescaline Analogues Containing Piperazine or Homopiperazine Rings* Michael W. Majchrzak et al.

*Primary Examiner*—Robert T. Bond
*Assistant Examiner*—Philip I. Datlow
*Attorney, Agent, or Firm*—Oblon, Spivak, McClelland, Maier & Neustadt

[57] ABSTRACT

Diamine compounds of formula (I) or an addition salt thereof are provided:

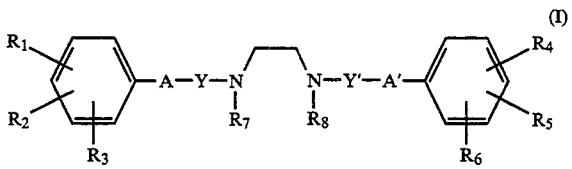

These compounds have an excellent cerebral protective action, are very safe, and exhibit a strong action when orally administered, and therefore, medicines containing such compounds are effective for treating disorders caused by cerebral hemorrhage, cerebral infarction, subarachnoid hemorrhage, transient ischemic attack, cerebrovascular disorders and the like, or preventing progress of such disorders.

7 Claims, No Drawings

DIAMINE COMPOUND AND BRAIN PROTECTING AGENT CONTAINING THE SAME

TECHNICAL FIELD

This invention relates to novel diamine compounds and acid addition salts thereof and cerebral protective drugs containing the compounds or their salts, and more particularly to diamine compounds and acid addition salts thereof which have an excellent cerebral protective action and are useful as an drug for treating disorders of cerebral functions or preventing the progress of such disorders, and to cerebral protective drugs containing the diamine compounds or their acid addition salts.

BACKGROUND ART

Recent increase of the population of senior citizens has brought about the increased number of patients suffering from various functional disorders of the brain, typified by those accompanied by cerebral hemorrhage, cerebral infarction, subarachnoid hemorrhage, transient ischemic attack, cerebrovascular disorders, and the like. These disorders are considered to be caused mainly from the decreased blood flow in the brain, hypoxia in the blood, metabolism disorders such as hypoglycemia.

Most of conventional drugs for treating these disorders have paid attention to the causes of the disorders to be treated, and have focused on the treatment of sequelae of cerebral ischemia, cerebrovascular dementia and the like. Such conventional drugs include drugs for improving cerebral circulation, drugs for improving cerebral metabolism, drugs for improving cerebral functions, drugs for inhibiting the platelet coagulation, which have already been clinically utilized. Recently, irrespective of the causes of the disorders, cerebral protective drugs have been proposed and have attracted attention as a drug for treating cerebral function disorders. They are designed to eliminate cerebral function disorders or preventing the progress of the disorders by protecting the brain from ischemia or hypoxia.

These drugs for treating cerebral function disorders, however, have only insufficient clinical effects, and do not show clear cerebral protective action when tested on animals under a condition of single dose oral administration, though most of them are designed to be useful for oral administration.

Accordingly, cerebral protective drugs which promise excellent clinical effect and are useful for oral administration have still been desired.

Under the above circumstances, the present inventors have conducted careful studies to solve the mentioned problems, and have found that the novel diamine compounds of formula (I) and their acid addition salts exhibit an excellent cerebral protective action, and this action is securely obtained even in the oral route administration. This invention was accomplished based on the above findings.

DISCLOSURE OF THE INVENTION

According to the present invention, there is provided diamine compounds represented by formula (I) and acid addition salts thereof:

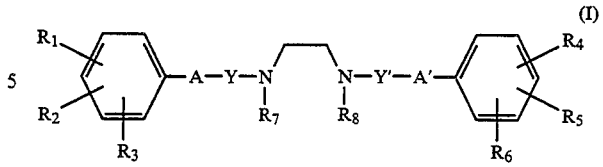

wherein R1, R2, R3, R4, R5 and R6 are the same or different from each other and represent individually a hydrogen atom, halogen atom, hydroxyl group, lower alkyl group, lower alkoxy group, lower acyloxy group, lower alkoxycarbonyloxy group, lower alkylsulfonyloxy group or an amino group, among which the lower alkyl group and lower alkoxy group may be substituted by a halogen atom or a phenyl group; R7 and R8 are the same or different from each other and represent individually a lower alkyl group, or the two bind to each other to represent an alkylene group having 1 to 4 carbon atoms; A and A' are the same or different from each other and represent individually a single bond, —O—, —NH—, —NHCO→, —CONH→, —NHCOO→, —NHCONH—, —SO$_2$NH→ or —COS→ (here, the symbol '→' denotes a bond to Y or Y'), Y and Y' are the same or different from each other and represent a lower alkylene group or lower alkenylene group; and cerebral protective drugs containing them as an active component.

The compounds (I) according to the present invention have an excellent cerebral protective action, are very safe and exhibit their strong action even in the oral route administration, thus useful as a cerebral protective drug.

BEST MODE FOR CARRYING OUT THE INVENTION

In formula (I), the lower alkyl groups represented by R1 to R8 are preferably those having 1 to 6 carbon atoms, and especially, those having a methyl group, ethyl group, n-propyl group, isopropyl group or the like are most preferred. Preferable alkyl groups in R1 to R6 which are a lower alkoxy group, lower acyloxy group, lower alkoxycarbonyloxy group or a lower alkylsulfonyloxy group are those having 1 to 6 carbon atoms, and preferable halogen atoms are fluorine, bromine, chlorine and the like. Preferable lower alkylene groups or lower alkenylene groups represented by Y or Y' are linear or branched groups having 1 to 8 carbon atoms.

Examples of the most preferable compounds (I) are represented by the following formula (I'):

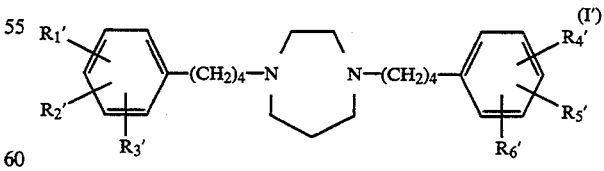

wherein R1' to R6' individually represent a lower alkoxy group.

The compounds (I) according to the present invention can be prepared by any of the following processes (1) to (9):

(1):

-continued (1):

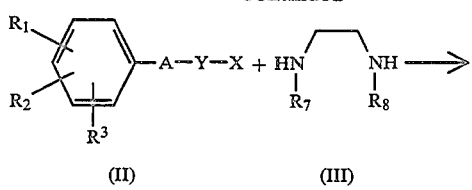

(II)    (III)

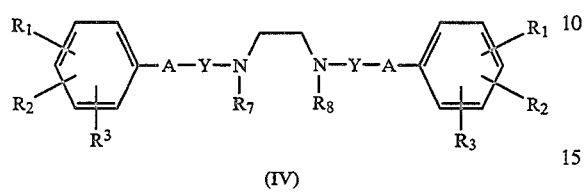

(IV)

wherein X represents a halogen atom, a mesyloxy group or a tosyloxy group, and R1 to R3, R7, R8, A and Y have the same meaning as defined hereinbefore.

According to this process, compounds (IV) of this invention can be prepared by the reaction between compounds (II) and ethylene diamine derivatives (III).

This process (1) is applicable for the preparation of compounds (IV) which are compounds (I) of the present invention where R1, R2, R3, A and Y are identical to R4, R5, R6, A' and Y', respectively. No limitations are imposed on the species of A (A') and Y (Y').

The reaction proceeds in the presence of a suitable solvent, preferably in the presence of a base, at room temperature up to 200° C. over several minutes to 10 hours. Examples of solvents useful in this process include ethers such as diethyl ether, dioxane, tetrahydrofuran; hydrocarbons such as chloroform, dichloromethane, carbon tetrachloride, benzene and toluene; alcohols such as methanol, ethanol and n-propanol; pyridine; dimethylformamide; dimethylsulfoxide; and water. Examples of bases include inorganic bases such as sodium carbonate, potassium carbonate, sodium hydroxide and potassium hydroxide; and organic bases such as triethylamine, diisopropylethylamine, di-t-butylamine, dimethylaminopyridine and pyrrolidinopyridine.

(2):

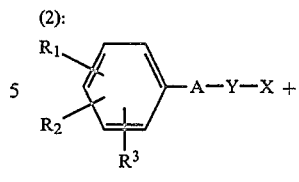

(II)

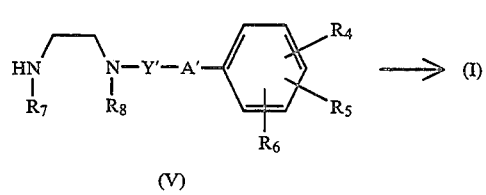

(V)

wherein R1 to R8, A, A', Y, Y' and X individually have the same meaning as defined hereinbefore.

According to this process (2), compounds (I) of this invention can be prepared by the reaction between compounds (II) and diamine derivatives (V).

This process (2) is applicable for the preparation of the target compounds (I) irrespective of their species. The reaction proceeds under the similar conditions as described in process (1) above.

(3):

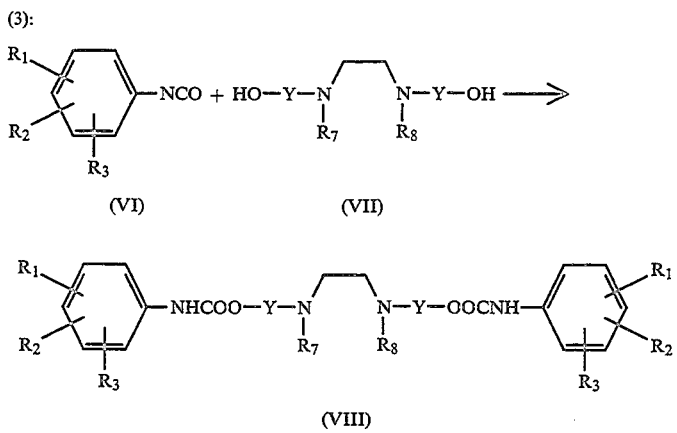

(VI)    (VII)

(VIII)

wherein R1 to R3, R7, R8 and Y have the same meaning as defined hereinbefore.

According to this process (3), compounds (VIII) of this invention which have an urethane bond can be prepared by the reaction between phenylisocianate derivatives (VI) and dihydroxyamines (VII). This process (3) is applicable for the preparation of compounds (VIII) which are compounds (I) where R1, R2, R3 and Y are identical to R4, R5, R6 and Y', respectively, and A and A' are —NHCOO—.

The reaction between compounds (VI) and compounds (VII) proceeds in a similar solvent as described in process (1), preferably in hydrocarbons, while being stirred under heat at 50° C. to 200° C. over 10 minutes to 5 hours. The starting material, phenylisocianate derivatives (VI) can be obtained by, for example, reacting the corresponding benzoyl halogenides with sodium azide.

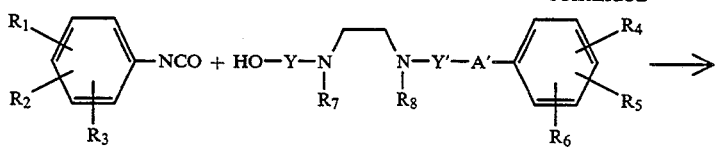

(VI)                    (IX)

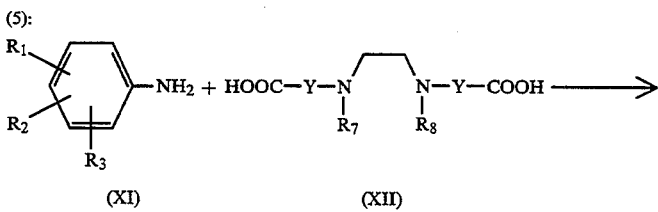

(X)

wherein R1 to R8, A', Y and Y' have the same meaning as defined hereinbefore.

According to this process (4), compounds (X) of this invention can be prepared by the reaction between phenylisocianate derivatives (VI) and alcohols (IX). This process (4) is applicable for the preparation of compounds (X) which are compounds (I) of the present invention where A is —NHCOO—. The reaction proceeds under the similar conditions as described in process (3).

(5):

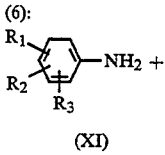

(XI)                    (XII)

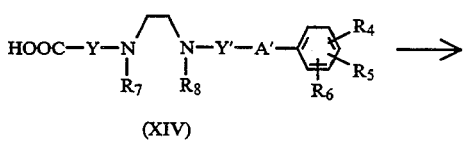

(XIII)

wherein R1 to R3, R7, R8 and Y have the same meaning as defined hereinbefore.

According to this process (5), compounds (XIII) of this invention can be prepared by the reaction between amines (XI) and carboxylic acids (XII). This process (5) is applicable for the preparation of compounds (XIII) which are compounds (I) of the present invention where R1, R2, R3 and Y are identical to R4, R5, R6 and Y', respectively, and A and A' are —NHCO—.

To carry out this reaction, a reaction for forming an acid amide, which is generally employed in the field of peptide synthesis, may be followed.

In detail, several reactions are mentioned which include (a): a reaction between free amine (XI) and free carboxylic acid (XII) in the presence of a condensing agent, (b): a reaction between free amine (XI) and a reactive derivative of carboxylic acid (XII) and (c): a reaction between a reactive derivative of amine (XI) and free carboxylic acid (XII). Examples of the condensing agents useful in the reaction (a) are dicyclohexyl carbodiimide, N,N'-disuccinimidylcarbamate, N,N'-carbonyldiimidazol and diphenylphosphorylazide. Conditions of the reaction may differ depending on the condensing agents employed, and when dicyclohexyl carbodiimide is used, reaction will complete by first allowing carboxylic acid (XII) and dicyclohexyl carbodiimide to react in a solvent, followed by the addition of amine (XI) and then stirring the mixture at −30° to 100° C. over several hours to several days. Any solvents which are mentioned in process (1) hereinbefore can be used. Examples of the reactive derivatives of carboxylic acids (XII) in process (b) include acid halides, acid anhydrides, acid mixture anhydrides, active esters and acid azides. Examples of the reactive derivatives of amine (XI) in process (c) include isocianate and phosphazo compounds.

(6):

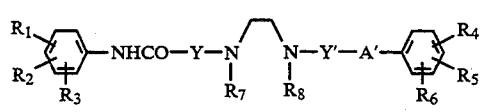

wherein R1 to R8, Y, Y' and A' have the same meaning as defined hereinbefore.

According to this process (6), compounds (XV) of this invention can be prepared by the reaction between amines (XI) and carboxylic acids (XIV). This process (6) is applicable for the preparation of compounds (XV) which are compounds (I) of the present invention where A is —NHCO—. The reaction may be carried out under the similar conditions as described in process (5).

(7):

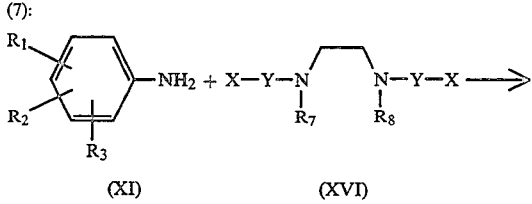

(XI)    (XVI)

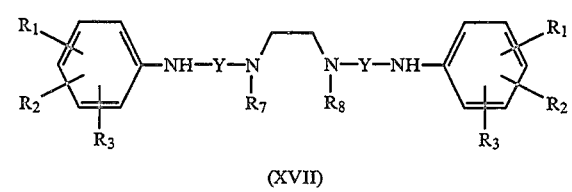

(XVII)

wherein R1 to R3, RT, R8, Y and X have the same meaning as defined hereinbefore.

According to this process (7), compounds (XVII) of this invention can be prepared by the reaction between amines (XI) and compounds (XVI)'. This process (7) is applicable for the preparation of compounds (XVII) where R1, R2, R3 and Y are identical to R4, R5, R6 and Y', respectively, and A and A' are —NH—.

This reaction is carried out by allowing amines (XI) and compounds (XVI) to react in a similar solvent as described in process (1) while stirring at −30° to 200° C. over 1 to 20 hours.

(8):

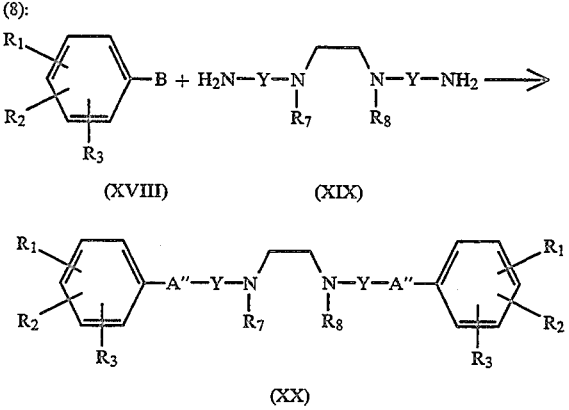

(XVIII)    (XIX)

(XX)

wherein B represents COX', SO₂X' (here, X' is a halogen atom) or NCO, A" represents —CONH—, —SO₂NH— or —NHCONH—, and R1 to R3, R7, R8 and Y individually have the same meaning as defined hereinbefore.

According to this process (8), compounds (XX) of this invention can be prepared by the reaction between compounds (XVIII) and amines (XIX). This process (8) is applicable for the preparation of compounds (XX) which are compounds (I) where R1, R2, R3 and Y are identical to R4, R5, R6 and Y', respectively, and A and A' are —CONH—, —SO₂NH— or —NHCONH—.

This reaction is carried out by allowing compounds (VIII) and amines (XIX) to react in a similar solvent as described in process (1) while stirring at −30° to 100° C. over 10 minutes to 10 hours.

(9):

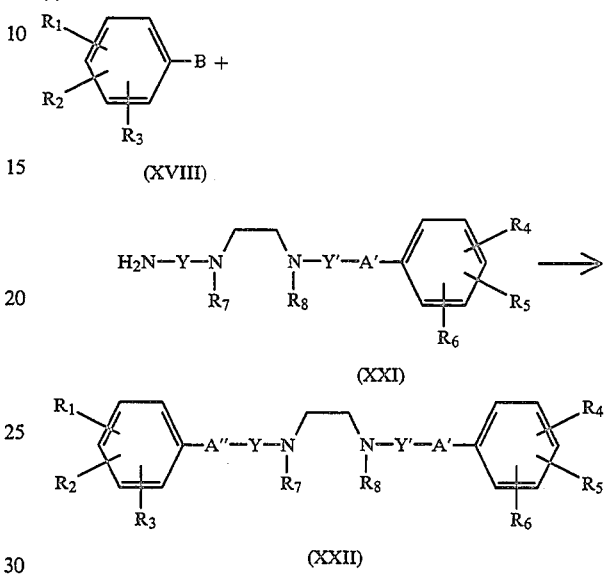

(XVIII)

(XXI)

(XXII)

wherein R1 to R8, A', A", Y, Y' and B have the same meaning as defined hereinbefore.

According to this process (9), compounds (XXII) of this invention can be prepared by the reaction between compounds (XVIII) and amines (XXI). This process (9) is applicable for the preparation of compounds (XXII) which are compounds (I) where A is —CONH—, —SO₂NH— or —NHCONH—. The reaction is carried out under the similar conditions as in process (8).

When compounds (I) are prepared in accordance with any of the processes (1) to (9) above, and if R1 to R6 contain an amino group, corresponding nitro compounds may be subjected to the reaction, followed by the reduction of the nitro group by a conventional method. Moreover, R1 to R6, which are hydroxyl group, lower acyloxy group and lower alkoxycarbonyloxy group, can mutually be converted with each other by a conventional method.

The obtained compounds (1) according to this invention can be isolated and purified by a conventional method, and preferably, salt exchange, extraction with solvent and chromatography are suitably combined and applied as desired.

The compounds (I) of this invention which are obtainable from the above processes can be converted to acid addition salts by a method known per se as desired. Examples of useful acids include inorganic acids such as sulfuric acid, hydrochloric acid, nitric acid, phosphoric acid, and hydrobromic acid, and organic acids such as acetic acid, lactic acid, succinic acid, tartaric acid, malic acid, maleic acid, citric acid, fumaric acid, methanesulfonic acid and toluenesulfonic acid.

The thus obtained compounds (I) or their acid addition salts of this invention exhibit an excellent cerebral protective action and have low toxicity.

In order to use compounds (I) of this invention as a medicine, they may be formed into tablets, capsules, granules, powder, injections, suppositories, etc. by the use of suitable excipients, carriers, diluents and the like and orally or non-orally administered, with oral administration being particularly preferred. Preparation is effected by methods known per se. For example, preparations for oral administration may be carried out by formulating compounds (I) of this invention with excipients such as starch, mannitol and lactose; binders such as sodium carboxylmethylcellulose and hydroxypropylcellulose; deregulators such as crystalline cellulose and carboxymethylcellulose; lubricant such as talc, magnesium stearate; fluidity modifiers such as silicic acid anhydride in a suitable combination. Injection preparations are also obtainable by a conventionally known process.

The compounds (I) of this invention are preferably administered via oral route with a dosage of 10 to 3,000 mg per day which is divided to 1 to 3 times, though there may be variations depending on the age and symptoms of the patients.

When the compounds (I) of this invention are administered by injection, the preferable manner of use is an intravenous injection at the dosage of 0.1 to 1000 mg of compounds per day, which is divided to 1 to 3 times.

EXAMPLES

This invention will now be described in detail by way of Examples.

Example 1

Preparation of N,N'-bis-[4-(3,4,5-trimethoxyphenyl)-butyl]homopiperazine.2HCl:

7.5 g of 1-chloro-4-(3,4,5-trimethoxyphenyl)butane, 1.3 g of homopiperazine, 4.5 g of potassium carbonate and 5.3 g of potassium iodide were added to 42 ml of dimethylformamide and stirred at 100° C. for 1 hour. The reaction mixture was added to an aqueous NaCl solution, followed by extraction with ethyl acetate. The ethyl acetate layer was extracted with a diluted hydrochloric acid, and the aqueous layer was washed with ethyl acetate. Subsequently, NaOH was added thereto to control the pH to basic, and extracted with ether. The ether layer was washed with an aqueous NaCl solution, dried, and the solvent was evaporated. The residue was purified by silica gel column chromatography to obtain 4.7 g of a free base.

The obtained free base was converted to a hydrochloride by a conventional method, and recrystallized from methanol-ether to obtain 3.2 g of the target compound having a melting point of 191° to 194° C. (decomposed).

$^1$H—NMR (CDCl$_3$);δ2.60 (4H, br,t, J=8 Hz) 3.82 (6H, s) 3.86 (12H, s) 6.37 (4H, s)
IR (KBr); cm$^{-1}$ 1587, 1238, 1122

Example 2

Preparation of N,N'-bis-[(E)-4-(3,4,5-trimethoxyphenyl)-3-butenyl]homopiperazine.2HCl:

Procedure of Example 1 was followed using 1.37 g of (E)-4-(3,4,5-trimethoxyphenyl)-3-butenylbromide to obtain 619 mg of a free base. The obtained free base was converted to a hydrochloride by a conventional method, and subsequently precipitated with dioxane-ether to obtain 534 mg of the target compound as a pale yellow amorphous substance.

$^1$H-NMR (CDCl$_3$);δ3.80 (6H, s), 3.88 (12H, s) 6.53 (2H, d, J=15.6 Hz) 6.76 (4H, s)
IR (KBr); cm$^{-1}$ 1580, 1502, 1451, 1416

Examples 3 to 8

The following compounds were prepared following either procedure of Example 1 or Example 2.

Example 3

N,N'-dimethyl-N,N'-bis-[3-(3,4,5-trimethoxyphenylcarbamoyl) propyl]ethylene diamine.2 maleic acid:
Melting point: 159° to 161° C. $^1$H-NMR (CDCl$_3$+DMSO-d$_6$); δ2.68 (6H, s) 3.76 (6H, s) 3.80 (12H, s) 6.27 (4H, s) 6.96 (4H, s)
IR (KBr); cm$^{-1}$ 1690, 1615, 1412, 1123

Example 4

N,N'-bis-[4-(3,4,5-trimethoxyphenyl) propyl]-homopiperazine.2 maleic acid:
Melting point: 137° to 139° C. $^1$H-NMR (CDCl$_3$); δ3.81 (3H, s) 3.84 (6H, s) 6.26 (4H, s) 6.39 (4H, s)
IR (KBr); cm$^{-1}$ 1587, 1497, 1124, 861

Example 5

N,N'-bis-[(Z)-4-(3,4,5-trimethoxyphenyl)-3-butenyl]-homopiperazine.2HCl:
Amorphous powder, $^1$H-NMR(CD$_3$OD): δ3.78 (6H, s) 3.95 (12H, s) 6.49 (2H, d, J=10 Hz) 6.55 (4H, s)
IR (KBr); cm$^{-1}$ 1577, 1502, 1456

Example 6

N,N'-bis-[3-(3,4,5-trimethoxybenzoylthio)propyl]-homopiperazine.2HCl
Melting point: 214° to 216° C. (decomposed) $^1$H-NMR (CDCl$_3$); δ2.61 (2H, m) 3.95 (18H, s) 7.24 (4H, s)
IR (KBr); cm$^{-1}$ 1650, 1583, 1449, 1410

Example 7

N,N'-dimethyl-N,N'-bis-[3-(3,4,5-trimethoxybenzoylthio)propyl]ethylenediamine.2HCl:
Melting point: 193° to 195° C. $^1$H-NMR(DMSO-d$_6$); δ2.87 (6H, s) 3.79 (6H, s) 3.88 (12H, s) 7.18 (4H, s)
IR (KBr); cm$^{-1}$ 1661, 1584, 1231, 1124

Example 8

N,N'-bis-[5-(3,4,5-trimethoxyphenyl)-n-pentyl]-homopiperazine.2HCl
Amorphous powder $^1$H-NMR(CD$_3$OD); δ2.60 (4H, t, J=7 Hz) 3.70 (6H, s) 3.80 (12H, s) 6.49 (4H, s)
IR (KBr); cm$^{-1}$ 1585, 1503, 1455, 1420

Example 9

Preparation of N,N'-bis-[3-(3,4,5-trimethoxyphenylcarbamoyl) propyl]homopiperazine.2 maleic acid: 7.2 g of ` N-[3-(3,4,5-trimethoxyphenylcarbamoyl)propyl]-homopiperazine, 2.8 g of potassium carbonate and 3.4 g of potassium iodide were added to 10 ml of dimethylformamide, and 5.7 g of 1-chloro-3-(3,4,5-trimethoxyphenylcarbamoyl)propane was added thereto under stirring at 70° C., followed by a stirring for 30 minutes at the same temperature, and further stirring for 30 minutes at 80° C. 5.9 g of the above chloro compounds and 2.8 g of potassium carbonate were added thereto, and the mixture was stirred for 30 minutes at 80° C. The reaction mixture was dissolved in ethyl acetate, washed with water, and extracted with a diluted hydrochloric acid. pH was controlled to basic with NaOH, and extraction was carried out with chloroform. The chloroform layer was washed with water, dried, followed by the evaporation of solvent to obtain a 20.1 g of a crude product. This product was purified by silica gel column chromatography, converted to a maleate by a conventional method, and recrystallized from methanol-ether to obtain 5.5 g of the target compound.

Melting point: 181° to 184° C. $^1$H-NMR (CDCl$_3$+DMSO-d$_6$); δ3.77 (6H, s) 3.83 (12H, s) 6.27 (4H, s) 6.99 (4H, s)

IR (KBr); cm$^{-1}$ 1644, 1505, 1229, 1124

Example 10

Preparation of N-[5-(3,4,5-trimethoxyphenyl)pentyl]-N'-[3-(2,6-dimethyl-4-hydroxyphenylcarbamoyl)-propyl]homopiperazine:

1.0 g of 1-[(3,4,5-trimethoxyphenyl)pentyl]homopiperazine and 1.4 g of 1-chloro-3-(2,6-dimethyl-4-hydroxyphenylcarbamoyl)propane were allowed to react and processed in a similar manner as described in Example 9 to obtain 0.6 g of the target compound.

Oily substance $^1$H-NMR(CDCl$_3$); δ2.08 (6H, s) 2.84 (9H, s) 6.35 (2H, s) 6.42 (2H, s)

IR (CHCl$_3$); cm$^{-1}$ 3320, 1652, 1588, 1401

Example 11

Preparation of N-[5-(3,4,5-trimethoxyphenyl)pentyl]-N'-[3-(4-acetyloxy-2,6-dimethylphenylcarbamoyl)propyl]-homopiperazine.2 maleic acid:

The compound obtained in Example 10 was converted to an oxalate by a conventional method, and subsequently acetylated with acetic anhydride and pyridine. By a conventional method, the acetylated product was converted to a maleate and recrystallized from ethanol-ether to obtain 4.8 g of the target compound.

Melting point: 85° to 89° C. (decomposed) $^1$H-NMR (CDCl$_3$+DMSO-d$_6$) 2.19 (6H, s) 2.27 (3H, s) 3.80 (3H, s) 3.85 (6H, s) 6.27 (4H, s) 6.79, 6.39 (2H, s) for each IR (KBr); cm$^{-1}$ 1750, 1207, 1121, 872

Example 12

Preparation of N,N'-bis-[4-(3,4,5trimethoxyphenyl)oxybutyl]homopiperazine.2 maleic acid:

711 mg of 1-[4-(3,4,5-trimethoxyphenyl)oxybutyl]-homopiperazine and 818 mg of 1-bromo-4-(3,4,5-trimethoxyphenyl)oxybutane were allowed to react and processed in the similar manner as described in Example 9 to obtain 785 mg of a free base. The obtained free base was converted to a maleate by a conventional method and recrystallized from methanol-ether to obtain 959 mg of the target compound.

Melting point: 124° to 126° C. $^1$H-NMR (CDCl$_3$); δ3.78, 3.83 (9H, s) for each 6.13 (4H, s) 6.25 (4H, s)

Examples 13 to 36

The following compounds were prepared according to the procedures of Examples 9, 10, 11 or 12 described above.

Example 13

N-[3-(3,4,5-trimethoxyphenylcarbamoyl)propyl]-N'-[3-(4-acetyloxy-2,6-dimethoxyphenylcarbamoyl)-propyl]-homopiperazine.2 maleic acid:

Amorphous powder $^1$H-NMR(DMSO-d$_6$); δ2.25 (3H, s) 3.60 (3H, s) 3.70, 3.72 (3H, s) for each 6.10 (4H, s) 6.48, 6.97 (2 H, s) for each IR (KBr); cm$^{-1}$ 1754, 1651, 1123, 997

Example 14

N-[3-(3,4,5-trimethoxyphenylcarbamoyl)propyl]-N'-[3-(4-hydroxy-2,6-dimethylphenylcarbamoyl)propyl]-homopiperazine:

Oily substance $^1$H-NMR(CDCl$_3$); δ2.05 (6H, s) 3.79 (6H, s) 3.80, (3H, s) 6.36, 6.89 (2 H, s) for each

Example 15

N-[3-(3,4,5-trimethoxyphenylcarbamoyl)propyl]-N'-[3-(4-acetyloxy-2,6-dimethylphenylcarbamoyl)propyl]-homopiperazine:

Oily substance $^1$H-NMR(CDCl$_3$); δ2.19 (6H, s) 2.27 (3H, s) 3.80 (3H, s) 3.83 (6H, s) 6.78, 6.92 (2 H, s,) for each IR(CHCl$_3$); cm$^{-1}$ 1749, 1609, 1223, 1128

Example 16

N-[3-(3,4,5-trimethoxyphenylcarbamoyl)propyl]-N,-[3-[4-(2-trifluoroethoxy)-2,6-dimethylphenylcarbamoyl]propyl]homopiperazine.2 maleic acid:

Melting point: 125° to 129° C. (decomposed) $^1$H-NMR(DMSO-d$_6$); δ2.11 (6H, s) 3.61 (3H, s) 3.73 (6H, s) 4.69 (2H, q, J=9 Hz) 6.10 (4H, s) 6.78, 6.98 (2 H, s) for each IR(KBr); cm$^{-1}$ 3476, 1662, 1509, 1124

Example 17

N-[3-(3,4,5-trimethoxyphenylcarbamoyloxy)propyl]-N'-[3-[4-(2-trifluoroethoxy)-2,6-dimethylphenylcarbamoyl]propyl]homopiperazine.2HCl:

Amorphous powder $^1$H-NMR(DMSO-d$_6$); δ2.11 (6H, s) 3.60 (3H, s) 3.72 (6H, s) 4.70 (2H, q, J=9 Hz) 6.79, 6.85 (2H, s) for each IR (KBr); cm$^{-1}$ 3398, 1716, 1645, 1605

Example 18

N,N'-bis-[3-[4-(2-trifluoroethoxy)-2,6-dimethylphenylcarbamoyl]propyl]homopiperazine.2HCl:

Melting point: 231° to 233° C. $^1$H-NMR (DMSO-d$_6$); δ2.11 (12H, s) 4.69 (4H, J=9 Hz) 6.78 (4H, s)

IR(KBr); cm$^{-1}$ 3397, 1645, 1277, 1160

Example 19

N,N'-bis-[4-(3,4,5-trimethoxyphenylcarbamoyl)-butylhomopiperazine.2 maleic acid:

Melting point: 138° to 141° C. $^1$H-NMR (CDCl$_3$+DMSO-d$_6$); δ3.77 (6H, s) 3.84 (12H, s) 6.26 (4H, s) 7.01 (4H, s)

IR (KBr); cm$^{-1}$ 3321, 1684, 1610, 1124

Example 20

N-[3-(2,4,6-trimethoxyphenylcarbamoyl)propyl]-N'-[3-(3,4,5-trimethoxyphenylcarbamoyl)propyl]homopiperazine:

Oily substance $^1$H-NMR(CDCl$_3$); δ3.77, 3.80, 3.82 (6H, s) for each 6.09, 6.85 (2H, s) for each IR (CHCl$_3$); cm$^{-1}$ 1671, 1604, 1506, 1129

Example 21

N,N'-bis-[3-(2,4,6-trimethoxyphenylcarbamoyl)-propyl]homopiperazine:

Oily substance $^1$H-NMR(CDCl$_3$); δ3.78 (12H, s) 3.80 (6H, s) 6.14 (4H, s)

IR (CHCl$_3$); cm$^{-1}$ 1668, 1608, 1507, 1130

Example 22

N-[3-(4-acetyloxy-2,6-dimethylphenylcarbamoyl)-propyl]-N'-[3-(2,4,6-trimethoxyphenylcarbamoyl)-propyl]homopiperazine.2 maleic acid:

Melting point: 60° C. (decomposed) $^1$H-NMR(CDCl$_3$+DMSO-d$_6$); δ2.18 (6H, s) 2.27 (3H, s)

3.76 (6H, s) 3.79 (3H, s) 6.31 (4H, s) 6.77, 6.12 (2 H, s) for each

IR (KBr); cm⁻¹ 3647, 1511, 1361, 1203

Example 23

N-[3-(4-acetyloxy-2,6-dimethylphenylcarbamoyl)-propyl]-N'-[3-(4-methoxy-2,6-dimethylphenylcarbamoyl)propyl]-homopiperazine.2 maleic acid:

Melting point: 90° C. (decomposed) ¹H-NMR (CDCl₃+DMSO-d₆); δ2.16, 2.18 (6 H, s) for each 2.28 (3H, s) 3.76 (3H, s) 6.30 (4H, s) 6.59, 6.78 (2 H, s) for each IR (KBr); cm⁻¹ 3232, 1750, 1650, 1576

Example 24

N,N'-bis-[3-(4-acetyloxy-2,6-dimethylphenylcarbamoyl)propyl]homopiperazine.2 maleic acid:

Melting point: 80° C. (decomposed) ¹H-NMR(CDCl₃+DMSO-d₆); δ2.20 (12H, s) 2.29 (6H, s) 6.29 (4H, s) 6.79 (4H, s)

IR (KBr); cm⁻¹ 3474, 1750, 1655, 1207

Example 25

N-[3-(2,4,6-trimethoxyphenylcarbamoyl)propyl] -N'-[3-(4-methoxy-2,6-dimethylphenylcarbamoyl)propyl]-homopiperazine. 2 maleic acid:

Melting point: 85° C. (decomposed ) ¹H-NMR (CDCl₃+DMSO-d₆); δ2.16 (6H, s) 3.76 (6H, s) 3.77, 3.80 (3H, s) for each 6.28 (4H, s) 6.14, 6.59 (2H, s) for each IR (KBr); cm⁻¹ 3338, 1652, 1591, 1203

Example 26

N,N'-bis[3-(4-methoxy-2,6-dimethylphenylcarbamoyl)propyl ]homopiperazine:

Melting point: 158° to 161° C. ¹H-NMR (CDCl₃+DMSO-d₆); δ2.20 (12H, s) 3.77 (6H, s) 6.60 (4H, s)

IR (KBr); cm⁻¹ 3268, 1647, 1603, 1149

Example 27

N-[3-(4-methoxy-2,6-dimethylphenylcarbamoyl)propyl] -N,-[2-(3,4,5-trimethoxyphenyl)ethyl]homopiperazine:

Melting point: 94° to 96° C. ¹H-NMR (CDCl₃); δ2.24 (6H, s) 3.80 (3H, s) 3.90 (9H, s) 6.48, 6.71 (2 H, s) for each IR (KBr); cm⁻¹ 302, 1654, 1587, 1127

Example 28

N-[3-(4-methoxy-2,6-dimethylphenylcarbamoyl)propyl]N'-[3-(3,4,5-trimethoxyphenyl)propyl]homopiperazine:

Oily substance ¹H-NMR (CDCl₃); δ2.19 (6H, s) 3.78 (3H, s) 3.86 (9H, s) 6.45, 6.66 (2 H, s) for each IR (CHCl₃); cm⁻¹ 650, 1589, 1232, 1124

Example 29

N-[3-(4-hydroxy-2,6-dimethylphenylcarbamoyl)propyl]N'-[3-(3,4,5-trimethoxyphenylcarbamoyl)propyl]homopiperazine:

Oily substance ¹H-NMR (CDCl₃); δ2.08 (6H, s) 3.82 (3H, s) 3.83 (6H, s) 6.34, 6.38 (2 H, s) for each IR (Film); cm⁻¹ 235, 1648, 1235, 1124

Example 30

N-[3-(4-hydroxy-2,6-dimethoxyphenylcarbamoyl)-propyl]-N'-[3-(2,4,6-trimethoxyphenylcarbamoyl)-propyl]homopiperazine:

Amorphous powder ¹H-NMR (CDCl₃); δ3.64, 3.77 (6H, s) for each 3.79 (3H, s) 5.88, 6.13 (2 H, s) for each IR(CHCl₃); cm⁻¹ 656, 1597, 1153, 1130

Example 31

N-[3-(4-acetyloxy-2,6-dimethoxyphenylcarbamoyl)-propyl]-N'-[3-(2,4,6-trimethoxyphenylcarbamoyl)propyl] -homopiperazine.2 maleic acid:

Amorphous powder ¹H-NMR (CDCl₃+DMSO-d₆); δ2.26 (3H, s) 3.71 (12H, s) 3.78 (3H, s) 6.10 (4H, s) 6.24, 6.51 (2 H, s) for each IR (KBr); cm⁻¹ 374, 1755, 1646, 1124

Example 32

N-[3-(4-benzyloxy-2,6-dimethylphenylcarbamoyl)-propyl ]-N'-[2-(3,4,5-trimethoxyphenyl)ethyl]homopiperazine:

Oily substance ¹H-NMR(CDCl₃); δ2.22 (6H, s) 3.86 (3H, s) 3.88 (6H, s) 5.06 (2H, s) 6.46, 6.78 (2 H, s) for each IR(CHCl₃); cm⁻¹ 1661, 1589, 1486, 1461

Example 33

N-[3-(4-benzyloxy-2,6-dimethylphenylcarbamoyl)-propyl]-N'-[5-(3,4,5-trimethoxyphenyl)-n-pentyl]-homopiperazine:

Oily substance ¹H-NMR (CDCl₃); δ2.22 (6H, s) 3.88 (9H, s) 5.06 (2H, s) 6.46, 6.78 (2H, s) for each IR (CHCl₃); cm⁻¹ 1661, 1589, 1486, 1461

Example 34

N-[3-(4-mesyloxy-2,6-dimethylphenylcarbamoyl)-propyl]-N'-[5-(3,4,5-trimethoxyphenyl)-n-pentyl]-homopiperazine:

Oily substance ¹H-NMR (CDCl₃); δ2.26 (6H, s) 3.36 (3H, s) 3.86 (3H, s) 3.90 (6H, s) 6.46, 7.08 (2 H, s) for each IR (CHCl₃); cm⁻¹ 2924 , 1662, 1588, 1476

Example 35

N-methyl-N-[3-(3,4,5-trimethoxyphenylcarbamoyl)-propyl]-N'-methyl-N'-[3-(3,4,5-trimethoxybenzoylthio)propyl]ethylenediamine.2 maleic acid:

Melting point: 137° to 139° C. ¹H-NMR (CDCl₃+DMSO-d₆); δ2.65, 2.76 (3H, s) for each 3.78, 3.90 (3H, s) for each 3.83, 3.91 (6H, s) for each 6.28 (4H, s) 6.98, 7.19 (2H, s) for each IR (KBr); cm⁻¹ 660, 1582, 1355, 1126

Example 36

N-[3-(3,4,5-trimethoxyphenylcarbamoyl)propyl]-N'-[3(3,4,5-trimethoxyphenyl)propyl]homopiperazine.2 maleic acid:

Melting point: 89° to 91° C. ¹H-NMR (CDCl₃+DMSO-d₆); δ2.23 (3H, s) 2.16 (6H, s) 3.78 (3H, s) 6.24 (4H, s)

IR (KBr); cm⁻¹ 1754, 1653, 1616, 1123

Example 37

Preparation of N,N'-bis-[3-(4aminophenylcarbamoyloxy)propyl]homopiperazine:

1 g of p-nitrobenzoylchloride was dissolved in 22 ml of acetone, to which was added a solution of sodium azide in 5.2 ml of water while stirring in an ice bath, followed by stirring for 1 hour at the same temperature. Acetone was distilled off from the reaction mixture, and the residue was added with chloroform to dissolve, washed with water, dried, and chloroform was evaporated to obtain a crude acid azide compound. This compound was added with 20 ml of toluene and heated at 100° C. for 3 minutes, and subsequently, 520 mg of N,N'-bis-(3-hydroxypropyl)homopiperazine was added and stirred at 100° C. for 1 hour. The obtained nitro compounds were reduced with tin dichloride and HCl by a conventional method to obtain 507 mg of the target compound.

Amorphous powder: $^1$H-NMR (CDCl$_3$); δ4.13 (4H, t, J=6 Hz) 6.63, 7.14 (4H, d, J=9 Hz) for each
IR (CHCl$_3$); cm$^{-1}$ 3423, 1710, 1516, 825

Examples 38 to 45

The following compounds were prepared in the similar manner as described in Example 37.

Example 38

N,N,-bis-[2-(3,4,5-trimethoxyphenylcarbamoyloxy)ethyl]homopiperazine.2 maleic acid:
Melting point: 140° to 143° C. $^1$H-NMR (CDCl$_3$+CD$_3$OD); δ3.80 (6H, s) 3.84 (12H, s) 6.28 (4H, s) 6.80 (4H, s)
IR (KBr); cm$^{-1}$ 472, 1726, 1607, 1123

Example 39

N,N'-bis-[3-(3,4,5-trimethoxyphenylcarbamoyloxy)propyl]homopiperazine:
Oily substance $^1$H-NMR (CDCl$_3$); δ3.82 (18H, s) 4.24 (4H, t, J=6 Hz) 6.72 (4H, s)
IR (CHCl$_3$); cm$^{-1}$ 22, 1725, 1804, 1128

Example 40

N,N'-bis-[3-(4-hydroxy-3,5-dimethoxyphenylcarbamoyloxy)propyl]homopiperazine:
Amorphous powder: $^1$H-NMR (CDCl$_3$); δ3.84 (12H, s) 4.20 (4H, t, J=6 Hz) 6.72 (4H, s)
IR (CHCl$_3$); cm$^{-1}$ 518, 3424, 1720, 1623

Example 41

N,N'-bis-[3-(4-ethoxycarbonyloxy-3,5dimethoxyphenylcarbamoyloxy)propyl]homopiperazine:
Amorphous powder: $^1$H-NMR (CDCl$_3$); 1.36 (6H, t, J=8 Hz) 3.82 (12H, s) 6.74 (4H, s)
IR (CHCl$_3$); cm$^{-1}$ 3425, 1757, 1720, 1616

Example 42

N,N'-bis-[3-[4-(2-trifluoroethoxy) -3,5-dimethoxyphenylcarbamoyloxy)propyl]homopiperazine.2HCl:
Melting point: 211° to 214° C. (decomposed) $^1$H-NMR(DMSO-d$_6$); δ3.74 (12H, s) 4.36 (4H, q, J=10 Hz) 6.88 (4H, s)
IR (KBr); cm$^{-1}$ 3383, 1728, 1608, 1127

Example 43

N,N'-bis-[3-(4-fluorophenylcarbamoyloxy)propyl]-homopiperazine-2HCl:
Melting point: 204° to 207° C. (decomposed) $^1$H-NMR(DMSO-d$_6$); δ4.15 (4H, br,t, J=6 Hz) 7.10~7.30 (6H, m) 7.60~7.80 (2H, m)
IR (KBr);cm$^{-1}$ 3295, 1720, 1534, 1230

Example 44

N,N'-[3-(3-acetyloxy-4,5-dimethoxyphenylcarbamoyloxy)propyl]homopiperazine:
Oily substance $^1$H-NMR (CDCl$_3$); δ2.30 (6H, s) 3.78, 3.84 (6H, s) for each 6.66, 7.26 (2H, d, J=2 Hz) for each
IR (CHCl$_3$); cm$^{-1}$ 1761, 1726, 1507, 1193

Example 45

N,N'-[3-(4-acetyloxy-3,5-dimethoxyphenylcarbamoyloxy)propyl]homopiperazine:
Amorphous powder $^1$H-NMR (CDCl$_3$); δ2.32 (6H, s) 3.80 (12H, s) 4.24 (4H, t, J=6 Hz) 6.76 (4H, s)
IR (CHCl$_3$); cm$^{-1}$ 425, 1760, 1727, 1615

Example 46

Preparation of N-[2-(3,4,5-trimethoxyphenyl-carbamoyloxy) ethyl]-N'-[2-(4-acetyloxy-3,5-dimethoxyphenylcarbamoyloxy)ethyl]homopiperazine.2 maleic acid:

N-[2-(3,4,5-trimethoxyphenylcarbamoyloxy)ethyl]-N'-[2-hydroxyethyl)homopiperazine and 4-acetyloxy-3,5-dimethoxybenzoylchloride were reacted as described in Example 37. 307 mg of an acid azide obtained from this reaction was added to 10 ml of toluene and stirred at 100° C. for 1 hour. Solvent was evaporated from the reaction mixture, followed by purification by silica gel column chromatography [eluate: chloroform-methanol(30:1–20:1)]. 519 mg of a free base was obtained. The obtained material was converted to a maleate according to a conventional method to finally obtain 489 mg of the target compound as colorless powdery crystals.

Melting point: 103° to 107° C. (decomposed) $^1$H-NMR(DMSO-d$_6$); δ3.60 (3H, s) 3.70, 3.72 (6H, s) for each 6.14 (4H, s) 6.85, 6.91 (2 H, s) for each
IR (KBr); cm$^{-1}$ 1728, 1760 (shoulder), 1607, 1222

Examples 47, 48

Procedure of Example 46 was followed to prepare the following compounds.

Example 47

N-[3-(3,4,5-trimethoxyphenylcarbamoyloxy)-propyl]N'-[3-(3-acetyloxy-4,5-dimethoxyphenylcarbamoyloxy)propyl]homopiperazine:
Amorphous powder $^1$H-NMR (CDCl$_3$); δ2.31 (3H, s) 3.78, 3.80, 3.85 (3H, s) for each 3.84 (6H, s) 3.69 (4H, s)
IR (CHCl$_3$); cm$^{-1}$ 1760, 1725, 1510, 1196

Example 48

N-[3-(3,4,5-trimethoxyphenylcarbamoyloxy)propyl]-N'-[3-(3-hydroxy-4,5-dimethoxyphenylcarbamoyloxy)propyl]homopiperazine:
Amorphous powder $^1$H-NMR(CDCl$_3$); δ3.80 (3H, s) 3.83, 3.84 (6H, s) for each 6.48 (1H, d, J=2 Hz) 6.69 (3H, br,s)
IR (CHCl$_3$); cm$^{-1}$ 1723, 1606, 1508, 1128

Example 49

Preparation of N,N'-bis-[2-(3,4,5trimethoxyphenyl-carbamoyl)ethyl]homopiperazine:
852 mg of N,N'-bis-(2-carboxyethyl)homopiperazine was suspended in 25 ml of pyridine, and was added with 1.75 ml of dioxane solution of HCl (4 mmol/ml) under ice-cooling and stirring and then with 1.73 g of dicyclohexylcarbodiimide at 0° C. and stirred for further 2 hours. Subsequently, 1.92 g of 3,4,5-trimethoxyaniline was added thereto and stirred overnight at room temperature. After the reaction was completed, precipitates were filtered off, and the filtrate was condensed. The condensed filtrate was dissolved with a diluted hydrochloric acid and washed with ethyl acetate. The aqueous layer was neutralized and extracted with chloroform. The obtained extract was washed with water and dried for evaporation of the solvent. The obtained crude product was purified by preparative thin layer chromatography utilizing silica gel, and recrystallization from ethyl acetate-ether yielded 216 mg of the target compound as pale yellow prisms.

Melting point: 135° to 137° C. $^1$H-NMR(CDCl$_3$); $\delta$2.52 (4H, t, J=6 Hz) 6.91 (4H, s)

IR (KBr); cm$^{-1}$ 1677, 1603, 1506, 1234

Example 50

Preparation of N,N'-bis-[3-(3,4,5-trimethoxyanilino)propyl]piperazine.4HCl:

1.83 g of 3,4,5-trimethoxyaniline and 2.45 g of N,N'-bis-(3-bromopropyl) piperazine were dissolved in a mixture of 20 ml methanol, 3 ml of dimethylsulfoxide and 0.5 ml of water, and stirred under reflux over 7 hours. The reaction solution was condensed, made basic with NaOH, then extracted with chloroform. The chloroform layer was washed with an aqueous NaCl solution, followed by drying and evaporating the solvent. The residue was purified by silica gel column chromatography, and the obtained free base was converted to a hydrochloride by a conventional method. Recrystallization from methanol-ethanol yielded 350 mg of the target compound in pale brown prisms.

Melting point: 240° to 242 ° C. (decomposed ) $^1$H-NMR(DMSO-d$_6$); $\delta$3.63 (3H, s) 3.78 (6H, s) 6.64 (2H, br,s)

IR (KBr); cm$^{-1}$ 3389, 1613, 1506, 1243

Example 51

The procedure of Example 50 was followed to obtain the following compound:

N,N'-bis-[3-(3,4,5-trimethoxyanilino )propyl]homopiperazine. 4HCl:

Melting point: 214° to 216° C. (decomposed) $^1$H-NMR (CDCl$_3$+DMSO-d$_6$); $\delta$3.79 (34H, br,s) 7.08 (2H, br,s)

IR (KBr); cm$^{-1}$ 90, 1612, 1504, 1243

Example 52

Preparation of N,N'-bis-[3,(2,4,6-trimethoxybenzoylamino)propyl]homopiperazine.2 maleic acid:

13.1 g of N,N'-bis-(3-t-butoxycarbonylaminopropyl)-homopiperazine was dissolved in 136 ml of ethanol, and 26.8 ml of concentrated HCl was added thereto, followed by reflux for 30 minutes. After the reaction was completed, the resulting material was dried under reduced pressure. The residue was dissolved in chloroform, dried and the solvent was evaporated. The residual substance was dissolved in tetrahydrofuran, and filtered with Celite, followed by evaporation of solvent. The residue was dissolved in 299 ml of anhydrous pyridine, to which was added a solution which was prepared in advance by dissolving an acid chloride obtained from 13.4 g of 2,4,6-trimethoxy benzoic acid by a conventional method in 44 ml of benzene while cooling in an ice bath. The mixture was stirred for 3 hours at room temperature. After the reaction was completed, the solvent was evaporated and the residue was dissolved in chloroform followed by extraction with an aqueous 5% acetic acid solution. The aqueous layer was washed with chloroform, and made basic with sodium carbonate, and extracted with chloroform. The chloroform layer was washed and dried, and the crude product obtained after evaporation of the solvent was converted to maleate by a conventional method. Recrystallization from ethanol-acetone yielded 6.7 g of the target compound.

Melting point: 105° to 107° C. (decomposed) $^1$H-NMR (CDCl$_3$+DMSO-d$_6$); $\delta$3.78 (12H, s) 3.83 (6H, s) 6.23 (4H, s) 6.10 (4H, s)

IR (KBr); cm$^{-1}$ 3343, 1605, 1123, 861

Example 53

Preparation of N,N'-bis-[3-(3,4,5-trimethoxybenzenesulfonylamino)propyl]homopiperazine.2HCl:

Using 650 mg of 3,4,5-trimethoxybenzenesulfonyl chloride, the procedure of Example 52 was followed. 323 mg of a free base was obtained. This free base was converted to a hydrochloride, and recrystallized from methanol-ether to obtain 320 mg of the target compound as colorless powdery crystals.

Melting point: 223° to 227° C. (decomposed) $^1$H-NMR(DMSO-d$_6$); $\delta$3.73 (6H, s) 3.85 (12H, s) 7.09 (4H, s)

IR (KBr); cm$^{-1}$ 1591, 1411, 1315, 607

Example 54

Preparation of N,N'-bis-[3-[3-(3,4,5-trimethoxyphenyl)ureido]propyl]homopiperazine:

1.35 g of an acid azide compound obtained from 3,4,5-trimethoxybenzoylchloride by a similar method as described in Example 36 was dissolved in 16 ml dioxane, and stirred in a hot bath of 100° C. for 3 hours. After the mixture was cooled down to room temperature, a solution obtained by dissolving 550 mg of N,N'-bis-(3-aminopropyl)homopiperazine in 5 ml of dioxane was added thereto and stirred for two hours at room temperature. From the reaction mixture, solvent was evaporated and the residue was purified by alumina column chromatography to obtain 810 mg of the target compound as a vitreous substance.

$^1$H-NMR (CDCl$_3$); $\delta$3.80 (18H, br,s) 6.76 (4H, s)

IR (CHCl$_3$); cm$^{-1}$ 3326, 1655, 1546, 1117

Examples 55 to 58

The following compounds were prepared in accordance with a method described in Examples 52, 53 or 54.

Example 55

N+,N'-bis-[3-(3,4,5-trimethoxybenzoylamino)propyl]homopiperazine:

Melting point: 139° to 140° C. $^1$H-NMR (CDCl$_3$); $\delta$3.88 (18H, s) 7.06 (4H, s)

IR (KBr); cm$^{-1}$ 3255, 1627, 1581 , 1120

Example 56

N+,N'-bis-[3-(4-hydroxy-3,5-dimethoxybenzoylamino)propyl]homopiperazine:

Melting point: 205° to 207 ° C. (decomposed) $^1$H-NMR(DMSO-d$_6$); $\delta$3.80 (12H, s) 7.20 (4H, s)

IR (KBr); cm$^{-1}$ 3370, 1628, 1589, 1116

Example 57

N+,N'-bis-[3-(p-aminobenzoylamino)propyl]homopiperazine:

Amorphous powder $^1$H-NMR (CDCl$_3$); δ3.51 (4H, q, J=5 Hz) 6.64, 7.62 (4H, d, J=9 Hz)
IR (CHCl$_3$); cm$^{-1}$ 1620, 1497, 1283, 837

Example 58

N+,N'-bis-[3-(2,4,6-trimethoxybenzenesulfonylamino)propyl]homopiperazine:
Amorphous powder $^1$H-NMR(CDCl$_3$); δ3.02 (4H, t, J=7 Hz) 3.88, 3.92 (total 2 OH, s) 6.21 (4H, s)

Example 59

Preparation of N-[3-(3,5-dimethoxy-4-hydroxybenzoylamino)propyl]-N'-[3-(3,4,5-trimethoxybenzoylamino)propyl]homopiperazine:
510 mg of N-(3-aminopropyl)-N'-[3-(3,4,5-trimethoxybenzoylamino)propyl]homopiperazine and 378 mg of 3,5-dimethoxy-4-ethoxycarbonyloxybenzoyl chloride were reacted according to a conventional method to obtain 800 mg of an amide compound having a protected hydroxyl group.
This product was dissolved in 11 ml of methanol, added with 1.5 ml of 2N NaOH and stirred for 30 minutes at 60° C. After completion of the reaction, 580 mg of a crude product obtained by a conventional method was recrystallized from methanol-ether to obtain 500 mg of the target compound in pale yellow prisms.
Melting point: 147° to 150° C. $^1$H-NMR (CDCl$_3$); δ3.90 (15H, s) 7.10 (2H, s) 7.12 (2H, s)
IR (KBr); cm$^{-1}$ 3377, 3267, 1629, 1119

Examples 60–62

The following compounds were obtained in accordance with the procedure as described in Example 59.

Example 60

N-[3-(2-trifluoromethylbenzoylamino)propyl]-N'-[3-(3,4,5-trimethoxybenzoylamino)propyl]homopiperazine:
Oily substance $^1$H-NMR (CDCl$_3$); δ3.84 (3H, s) 3.90 (6H, s) 7.00 (2H, s)
IR (Film); cm$^{-1}$ 3272, 1639, 1545, 1123

Example 61

N-[3-(2,6-dimethoxy-4-hydroxybenzoylamino )propyl]-N'-[3-(2,4,6trimethoxybenzoylamino)propyl]homopiperazine:
Amorphous powder $^1$H-NMR (CDCl$_3$); δ3.74, 3.78 (6H, s) for each 3.81 (3H, s) 6.22, 6.08 (2 H, s) for each
IR (KBr); cm$^{-1}$ 3400, 1605, 1125

Example 62

N-[3-(4-acetyloxy-2,6-dimethoxybenzoylamino)propyl]-N'-[3-(2,4,6-trimethoxybenzoylamino)propyl]homopiperazine:
Amorphous powder $^1$H-NMR (CDCl$_3$); δ2.26 (3H, s) 3.77, 3.78 (6H, s) for each 3.80 (3H, s) 6.09, 6.30 (2H, s) for each
IR (CHCl$_3$); cm$^{-1}$ 1750, 1645, 1605, 1460

Example 63

Preparation of N-[3-(3,4,5-trimethoxyphenylcarbamoyl)propyl]-N'-[5-(3,4,5trimethoxyphenyl)-N-pentyl]homopiperazine:
515 mg of N-(3-carboxypropyl)-N'-[5-(3,4,5-trimethoxyphenyl)pentyl]homopiperazine was dissolved in 10 ml of anhydrous tetrahydrofuran, and 268 mg of 3,4,5-trimethoxyaniline and 301 mg of dicyclohexylcarbodiimide were added thereto while being stirred in an ice bath, followed by a further stirring at room temperature overnight. After completion of the reaction, isolation and purification were carried out according to a conventional method to obtain 551 mg of the target compound as an oily substance.
$^1$H-NMR (CDCl$_3$); δ3.86, 3.88 (total 18H, s) 6.45, 6.95 (2 H, s) for each
IR (CHCl$_3$); cm$^{-1}$ 670, 1602, 1501, 1430

Examples 64 to 65

The following compounds were obtained according to the procedure of Example 63.

Example 64

N-[3 -(3,4,5-trimethoxyphenylcarbamoyl)propyl]-N'-[2-(3,4,5-trimethoxyphenyl) ethyl]homopiperazine:
Oily substance $^1$H-NMR (CDCl$_3$); δ3.94 (9H, s) 6.44 (2H, s) 6.96 (2H, s)
IR (Film); cm$^{-1}$ 1674, 1602, 1541, 1504

Example 65

N-[3-(4-acetyloxy-2,6-dimethylphenylcarbamoyl)-propyl]-N'-[2-(3,4,5-trimethoxyphenyl)ethyl]homopiperazine:
Oily substance $^1$H-NMR (CDCl$_3$); δ2.24 , 2.30 (total 9H, s) 3.92 (9H, s) 6.50,6.90 (2 H, s) for each
IR (CHCl$_3$); cm$^{-1}$ 1749, 1665, 1588, 1418

Test Examples

Among the compounds (I) of this invention, typical compounds were tested with regard to the cerebral protective effect and toxicity.

(a) Anti-hypoxia action:
1) Effect of compounds on survival time under load of nitrogen gas:
Groups of male ddY mice, each mouse weighing 20 to 27 g and each group consisting of 10 mice, were provided. The compounds to be tested were prepared into a suspension of 0.5% methylcellulose and given to the mice by orally (indicated as p.o.) or intraperitoneally (indicated as i.p.). 60 Minutes after the oral administration, or 30 minutes after the peritoneal administration, a load of hypoxia was applied and the survival time was measured.
Anti-hypoxia test was carried out by placing one mouse in a 300 ml transparent plastic container, through which a mixture gas containing 95% nitrogen and 5% oxygen was passed at a flow rate of 80 l/hour. The gas was allowed to flow out of the container through a hole made in a side wall.
The survival time was defined to be a time span from the starting point of passing the mixture gas to the termination of respiratory movement of the mouse. The results were indicated as %difference of the survival time against untreated group of mice, which are shown in Table 1.
The statistic processing was carried out according to a Mean-Whitney U test.

TABLE 1

| Tested Compounds | Survival Time (%) | |
|---|---|---|
| (Example Nos.) | 3 mg/kg, p.o. | 100 mg/kg, p.o. |
| 1 | 94 | 69* |
| 9 | 131* | 113 |
| 11 | 125* | 126 |
| 52 | 141* | 133* |
| Idebenone | 113 (100 mg/kg, i.p.) | |

TABLE 1-continued

| Tested Compounds | Survival Time (%) | |
|---|---|---|
| (Example Nos.) | 3 mg/kg, p.o. | 100 mg/kg, p.o. |
| | | 99 (300 mg/kg, i.p.) |

\*: $p < 0.05$

2) Effect of compounds on survival time when potassium cianate was administered:

Groups of male ddY mice, each mouse weighing 23 to g and each group consisting of 10 mice, were provided. The compounds to be tested were prepared into a suspension of 0.5% methylcellulose and given to the mice by orally or intraperitoneally. 1 Hour after the oral administration, or 15 minutes after the intraperitoneal administration, 3 mg/kg of potassium cianate was injected via the caudal vein over 20 seconds. The time span from the startpoint of the injection of potassium cianate to the termination point of the respiratory movement was measured. The results were indicated as %difference of the survival time against untreated group of mice, which are shown in Table 2.

TABLE 2

| Tested Compounds (Example Nos.) | Survival Time (%) | | | |
|---|---|---|---|---|
| | 3 mg/kg, p.o. | 10 mg/kg, p.o. | 30 mg/kg, p.o. | 100 mg/kg, p.o. |
| 1 | 103 | 118* | 169* | |
| 9 | 103 | 114 | 120* | |
| 11 | | | 118 | 109 |
| 52 | | 109 | 132* | |
| Idebenone | | 111 (100 mg/kg, i.p.) | | |

\*: $p < 0.05$ (b) Effect against ischemic cerebral damage:

Groups of Slc:Wistar rats of about 10 weeks old, each group consisting of 4 to 5 rats were provided. Under etherization, the rats were cut open from the front neck on the median line, and the common carotid arteries in the both sides were detached to exposure, and ligated with surgical suture. 3.5 Hours after the ligation, the blood was allowed to recirculate without anesthesia.

The compounds to be tested had been subcutaneously given to the rats, each compound in an amount of 30 mg/kg, at 60 minutes and 30 minutes before the ligation. Idebenone, which was a control compound in this test, was also administered to rats under the same conditions in an amount of 150 mg/kg. The death rates at 72 hours after the recirculation are shown in Table 3.

TABLE 3

| Tested Compounds (Example Nos.) | Death Rate/ No. of samples |
|---|---|
| 1 | 1/5 |
| 9 | 0/4 |
| 11 | 0/4 |
| 52 | 0/5 |
| Non administration | 16/26 |
| Idebenone | 4/5 |

(c) Acute toxicity test:

Groups of male Slc:Wistar rats of about 10 weeks old were provided. The compounds to be tested were suspended in an aqueous 5% gum arabic and orally administered to the rats in an amount of 300 or 1000 mg/kg. The behavior of rats was observed at the time points of 0.5, 1, 2 and 4 hours after the oral administration, and the rats were fed and observed for further 3 days.

It was revealed that compounds of Examples 1, 9, 11 and 52 did not provoke any abnormal behavior of rats or death at the 1000 mg/kg oral dosage.

INDUSTRIAL APPLICABILITY

The compounds (I) according to the present invention have an excellent cerebral protective action, are very safe, and exhibit a strong action in oral route administration, and therefore useful as a cerebral protective drug. Accordingly, medicines containing the compounds are successfully applicable for treating disorders caused by cerebral hemorrhage, cerebral infarction, subarachnoid hemorrhage, transient ischemic attack, cerebrovascular disorders and the like, or preventing the progress of such disorders.

We claim:

1. A diamine compound of formula (I) or an acid addition salt thereof:

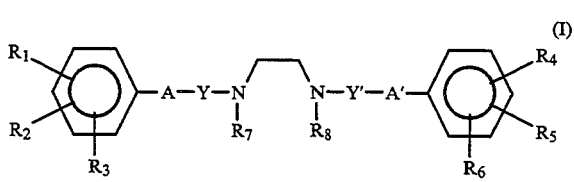

wherein $R_1$, $R_2$, $R_3$, $R_4$, $R_5$ and $R_6$ are the same or different from each other and represent individually a hydrogen atom, halogen atom, hydroxyl group, $C_{1-6}$ alkyl group, $C_{1-6}$ alkoxy group, $C_{1-6}$ acyloxy group, $C_{1-6}$ alkoxycarbonyloxy group, $C_{1-6}$ alkylsulfonyloxy group or an amino group, among which the alkyl group and alkoxy group may be substituted by a halogen atom or a phenyl group; $R_7$ and $R_8$ are combined to represent a trimethylene; A and A' are individually a single bond, Y and Y' are individually a tetramethylene.

2. A diamine compound of formula (I) or an acid addition salt thereof:

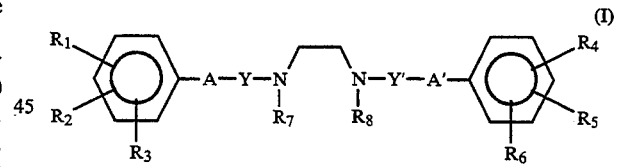

wherein $R_1$, $R_2$, $R_3$, $R_4$, $R_5$, and $R_6$ are the same or different from each other and represent individually a hydrogen atom, halogen atom, hydroxyl group, $C_{1-6}$ alkyl group, $C_{1-6}$ alkoxy group, $C_{1-6}$ acyloxy group, $C_{1-6}$ alkoxycarbonyloxy group, $C_{1-6}$ alkylsulfonyloxy group or an amino group, among which the alkyl group and alkoxy group may be substituted by a halogen atom or a phenyl group; $R_7$ and $R_8$ are combined to represent a trimethylene; A and A' are the same or different from each other and represent individually —O—, —NH—, —CONH→, —NHCOO→ or —SO$_2$NH→ wherein, the symbol '→' denotes a bond to Y or Y', Y and Y' are the same or different from each other and represent a $C_{1-8}$ alkylene group or $C_{2-8}$ alkenylene group.

3. The diamine compound or its acid addition salt as defined in wherein, in formula (I), $R_1$, $R_2$, $R_3$, $R_4$, $R_5$ and $R_6$ individually represent a $C_{1-6}$ alkoxy group, $R_7$ and $R_8$ are combined to represent a trimethylene, A and A' are individually a single bond, and Y and Y' are individually a tetramethylene.

4. A cerebral protective drug, comprising, as an active component, the diamine compound or its acid addition salt as defined in either claim 1 or 2.

5. A pharmaceutical composition comprising a compound of formula (I) as defined in either claim 1 or 2 and a pharmaceutical acceptable carrier.

6. A brain protecting method comprising administering an effective amount of a compound of formula (I) as defined in claims 1 or 2 to a subject in need thereof.

7. A method for treating disorders caused by cerebral hemorrhage, cerebral infarction, subarachnoid hemorrhage, transient ischemic attack, or cerebrovascular disorders, comprising administering an effective amount of a compound of formula (I) as defined in either claim 1 or 2 to a subject in need thereof.

* * * * *